United States Patent [19]

Gago et al.

[11] Patent Number: 4,915,943
[45] Date of Patent: Apr. 10, 1990

[54] COMPOSITIONS CONTAINING BIOSYNTHETIC PESTICIDE PRODUCTS, PROCESSES FOR THEIR PRODUCTION AND THEIR USE

[75] Inventors: Ignace Gago, Braine-l'Alleud; Lucien Charmoille, Brussels; Rene Detroz, Ohain, all of Belgium

[73] Assignee: Solvay & CIE (Société Anonyme), Brussels, Belgium

[21] Appl. No.: 244,384

[22] Filed: Sep. 14, 1988

[30] Foreign Application Priority Data

Sep. 14, 1987 [FR] France ................................ 87 12738

[51] Int. Cl.⁴ ..................... A61K 35/74; A61K 31/025
[52] U.S. Cl. ....................................... 424/93; 514/373; 435/170
[58] Field of Search ........................... 424/93; 514/373; 435/170

[56] References Cited

U.S. PATENT DOCUMENTS

| | | | |
|---|---|---|---|
| 3,065,123 | 11/1962 | Hinton et al. | 514/373 |
| 3,087,865 | 4/1963 | Drake et al. | 424/93 |
| 4,396,413 | 8/1983 | Miller et al. | 514/190 |
| 4,466,975 | 8/1984 | Magami et al. | 514/373 |
| 4,713,241 | 12/1987 | Wakisaka et al. | 424/93 |

FOREIGN PATENT DOCUMENTS

| | | |
|---|---|---|
| 1393646 | 2/1965 | France . |
| 2552627 | 4/1985 | France . |
| 428313 | 7/1967 | Switzerland . |
| 884541 | 12/1961 | United Kingdom . |

OTHER PUBLICATIONS

American Chemical Society, "Chemical Abstracts".

Primary Examiner—Johnnie R. Brown
Assistant Examiner—Jean C. Witz
Attorney, Agent, or Firm—Spencer & Frank

[57] ABSTRACT

The compositions contain a biosynthetic pesticide product, preferably originating from microorganisms of the genus Bacillus, in suspension in a liquid and at least one substance of general formula:

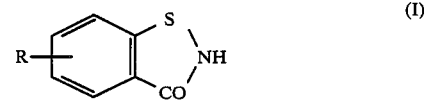

in which R represents a hydrogen atom, a halogen atom, or a salt derived from this substance.

The substance has a bacteriocidal or bacteriostatic action.

The compositions are effective against insects.

12 Claims, No Drawings

COMPOSITIONS CONTAINING BIOSYNTHETIC PESTICIDE PRODUCTS, PROCESSES FOR THEIR PRODUCTION AND THEIR USE

The present invention relates to compositions containing biosynthetic pesticide products as well as to processes for their production and their use.

Biosynthetic pesticide products have a great many advantages compared to chemical pesticides, especially on account of their high specificity. Thus, biosynthetic pesticides which are toxic or pathogenic to insects are generally non-toxic and non-pathogenic to man and other living creatures. In addition, given their specificity, they do not generally endanger the natural predators and parasites of the insects which it is desired to eliminate, nor the useful insects. They are not phytotoxic and do not leave any toxic residue. Finally, the insects do not appear to develop a resistance to this type of pesticide, contrary to what takes place on use of organic synthesis insecticides.

The biosynthetic pesticides can be obtained from a wide variety of microorganisms. Biosynthetic pesticide classes most commonly used in the fight against certain insects are obtained from Bacillus thuringiensis and Bacillus sphaericus, of which a large number of varieties are known.

Since the biosynthetic pesticides are not in general soluble, their application necessitates the use of particular techniques. They can be in the form of dry solid particles or in the form of suspensions of solid particles in a suitable liquid. In general, they are used in the form of suspensions which are sprayed onto the infected areas by various techniques which are known per se. One technique which is frequently used for treating large surface areas such as forests or large expanses of cultivated land, and also large areas of water, marshes or rivers, consists in spraying the biosynthetic pesticide suspensions from the air.

U.S. Pat. No. 3,087,865 has proposed the preparation of a biosynthetic pesticide composition which contains spores, inclusion bodies (crystals) and the soluble toxins originating from microorganisms of the genus Bacillus, such as Bacillus thuringiensis. These compositions can be in the form of suspensions or dry powders. It is thus possible to use the powder obtained by drying the filtration cake of the fermentation product (powder) optionally dispersed in water (cream) or a concentrate of the fermentation medium (paste). The compositions in liquid form (suspensions) can contain, inter alia, a fungicide or a bactericide compatible with the biosynthetic pesticide.

Similarly, French Pat. No. 1,393,646 has proposed the addition of bactericidal agents, such as xylene, or bacteriostatic compounds to biosynthetic pesticide compositions whose pH is set between 5.5 and 3.5.

However, although this addition of known bactericidal or bacteriostatic agents has given good results as regards the bactericidal effect obtained, it has not as yet made it possible to resolve critical problems necessary for obtaining good compositions which can be used in the field. Thus, it has not been possible, with the known bactericidal agents, to prepare stable compositions which maintain a good activity during storage and which at the same time make it possible to prevent the release of unpleasant odours produced during storage of the suspensions, nor to stop the swelling or retraction of the vessels containing the biosynthetic pesticide compositions. Similarly, it has not been possible to use the biosynthetic pesticide products at any pH, such as a neutral, slightly acid or slightly basic pH, despite the addition of a bactericidal or bacteriostatic agent. Moreover, the addition of certain compounds, such as xylene, in the biosynthetic compositions has been strongly discouraged, since this leads to compositions which are toxic to warm-blooded and/or cold blooded animals.

The present invention aims to provide compositions containing biosynthetic pesticide products having none of the disadvantages of the known compositions. It aims to provide compositions of biosynthetic pesticide products which are stable, which maintain a good activity during storage, which do not exhibit release of gas, and whose colour and viscosity do not alter in the course of time; the vessels containing these compositions do not swell and do not retract, even after a length storage period at ambient temperature or when the biosynthetic pesticide product has a neutral, slightly acid or slightly basic pH. It also aims to provide compositions in a position to receive the approval of the official agriculture departments, because they are in practice non-toxic to warmblooded and/or cold-blooded animals.

To this end, the invention relates to compositions containing biosynthetic pesticide products in the form of solid particles in suspension in a liquid and containing at least one substance of general formula (I):

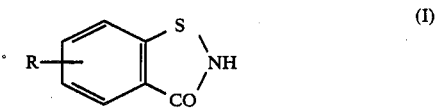

in which R represents a hydrogen atom, a halogen atom, or a salt deriving from this substance. In this case, it is preferable to work with alkaline metal salts, ammonium salts or salts of organic bases, or a radical containing a nitrogren atom.

The substances thus defined protect the biosynthetic pesticide products against contamination and alteration by microorganisms; they have a bactericidal or at least bacteriostatic function, preventing or stopping the proliferation of microorganisms such as bacteria.

In a preferred manner R represents hydrogen, chlorine, bromine or a salt deriving from the substance, especially an alkaline metal salt such as sodium or potassium, an ammonium salt or a salt of an organic base such as triethanolamine.

In a particularly preferred manner R represents hydrogen or chlorine. One substance according to the invention which has given good results is 1,2-benzisothia-zol-3-one (1,2-benzisothiazolin-3-one).

In the compositions according to the invention the substance is present in variable doses compatible with the particular biosynthetic pesticide product used. In general, its weight is between 0.0001 and 1.0 per cent of that of the biosynthetic pesticide product used. Its weight is usually between 0.001 and 0.5 per cent, and preferably between 0.01 and 0.2 per cent, of that of the biosynthetic pesticide product used.

The compositions according to the invention in the form of a suspension in a liquid containing water have a long storage life in a pH zone of between 3.5 and 8.5.

More particularly, the compositions of the invention can be used in acid pH zones of between pH 3.5 and 6.5, neutral pH zones of between pH 6.5 and 7.5, and basic pH zones of between pH 7.5 and 8.5. The result of this situation is that the compositions of the invention can be used by adjusting the pH to values situated in any one of the abovementioned zones. Moreover, this situation makes it possible to obtain stable compositions whose pH can evolve freely without it being necessary to take drastic measures to fix the pH in time. In short, this situation results in it being possible for the compositions according to the invention to be stored without danger for a longer period of time than the previously known compositions.

Biosynthetic pesticide products are understood to mean the biosynthetic pesticide products which make it possible to combat the animal and plant parasites of man, animals and plants (with the exception of microorganisms causing diseases in man and animals) and the vector agents of parasitic and viral diseases. These biosynthetic pesticides, also called biopesticides, can thus have a fungistatic or fungicidal action, also called anticryptogamic action, a herbicidal action or else an action against arthropods and, more particularly, against insects. The invention applies very particularly to the biosynthetic pesticides having an insecticidal or anticryptogamic action. Good results have been obtained with biosynthetic pesticides having an insecticidal action.

These biosynthetic pesticides can originate from various types of pathogenic organisms such as microorganisms (viruses, fungi, protozoa and bacteria) and nematodes. They can also originate from any microorganisms converted by insertion of DNA encoding for the production of toxins and originating from pathogenic microorganisms.

The biosynthetic pesticides can be present in the concentrated compositions according to the invention in a wide variety of forms. Thus, they can be in the form of the organisms themselves at any stage of their development, including the possible vegetative forms, as such, in combination with their culture medium, in a form having undergone complete or partial lysis, in a completely or partially sporulated form, in a form having partially or completely released the spores by various means such as bacterial autolysis, or in the form of the products which are excreted spontaneously by the organisms, such as the endotoxins, in the form of the products which it is possible to extract from these organisms, such as the endotoxins, by any method known per se involving or not involving lysis of the organism in question, in the form of the products possibly released by the organisms during certain stages of their development (crystals or endotoxins combined or not combined with the spores) or else in several of these forms simultaneously.

These different forms can optionally be combined with the residues of the culture medium. Good results have been obtained with the mixture containing the spores, the crystals or the endotoxins combined and, possibly, the exotoxins which forms spontaneously during autolysis of the bacterium at the end of sporulation. Such a mixture can contain, in addition to the spores, the crystals combined or not combined with the spores and the possible exotoxins, cells or cell debris as well as residual solid products from the nutrient medium used in the culture.

As bacterial microorganisms which are in general suitable as a source of biosynthetic pesticides, there may be mentioned the Eubacteriales of the class of the Sporulales and, more particularly, those of the order of the Bacillales, such as the Bacillaceae (for example the genus Bacillus). Among the latter, the bacterial microorganisms of the genus Bacillus such as Bacillus thuringiensis, Bacillus sphaericus, Bacillus popilliae, Bacillus cereus, Bacillus larvae, Bacillus lentimorbus, Bacillus fribourgensis and Bacillus penetrans are particularly suitable.

Good results have been obtained with Bacillus sphaericus and Bacillus thuringiensis of all serotypes and, more particularly, Bacillus sphaericus of serotypes 1a, 2a2b, 2a2c, 5a5b, 25, 26a26b, 26a26c and Bacillus thuringiensis of serotypes 1, 3a, 3a3b, 4, 6, 7, 8, 8a8b, 9, 10 and 14. The best results have been obtained with Bacillus sphaericus of serotypes 5a5b and 25 and Bacillus thuringiensis of serotypes 1 (thuringiensis variety), 3a3b (kurstaki variety), 6 (entomocidus variety), 7 (aizawa variety), 8a8b (morrisoni variety) and 14 (israelensis variety). The various types of Bacillus thuringiensis and Bacillus sphaericus can be used in the compositions according to the invention in the form of the microorganisms themselves, as such or lysed, their spores, endotoxins or crystals combined or not combined with their spores, or in several of these forms. These different forms can optionally be combined with residues of the culture medium. Good results have been obtained by using the mixture containing spores and the combined crystals which forms spontaneously during autolysis of the bacteria at the end of sporulation. Such a mixture can contain, in addition to the spores and the crystals combined or not combined with the spores, cells or cell debris as well as residual solid products from the nutrient medium used in the culture.

The compositions according to the invention can contain variable quantities of biosynthetic pesticides. In general they contain at least 3% and, more often, at least 5% by weight of biosynthetic pesticides. Their biosynthetic pesticide content does not in general exceed 90% and more often does not exceed 80% of their weight, without these values being critical.

The compositions according to the invention can additionally contain various other additives whose nature and function depend on the use of these compositions. They can contain perfumes or odour-masking agents, preservatives of various types such as antioxidants, especially BHT (butylated hydroxytoluene) and methyl parahydroxybenzoate, sugars such as sorbitol and agents capable of absorbing ultra-violet radiation (which could possibly cause the deactivation of the biosynthetic pesticide), fillers, pH-regulating agents, fixing agents, adhesives, baits, fatty substances, surfactants, dispersing or emulsifying agents such as amines, especially morpholine, diethanolamine or triethanolamine. They can also contain organic synthesis pesticides (chemical pesticides). In general, the additives comprise at least one preservative and at least one pH regulator. The preservatives are in general organic compounds.

Additives are mostly chosen which are soluble or dispersible in the solvent constituting the liquid phase. In general, additives are chosen which are soluble or dispersible in water.

The various additives are generally present in quantities not exceeding the weight of biosynthetic pesticides. They are mostly present in quantities of 0.01 to 50% of the weight of the biosynthetic pesticides.

The compositions according to the invention can also contain residues from the manufacture of the biosynthetic pesticide.

The compositions according to the invention are in the form of suspensions in a liquid. The latter must be inert with respect to the biosynthetic pesticides and, in particular, it must not deactivate them nor provoke their coagulation or any other physical alteration. The liquid can be made up of a single solvent or of a mixture of solvents. In general, the solvent contains water.

Good results have been obtained when the solvent contains at least 75% and, more often, at least 90% by weight of water. In general, the liquid present in the composition according to the invention is made up essentially of water. The other possible solvents are mostly the possible solvents of the surfactants or the possible solvents of the other additives. In general, these are common solvents such as alcohols and, more particularly, alcohols having 1 to 7 carbon atoms, such as, in particular, methanol and ethanol.

The compositions according to the invention generally contain an acid or acids such as tartaric acid, malic acid, citric acid, phosphoric acid, propionic acid, ascorbic acid, sorbic acid, oleic acid, or a mixture of two or more of these acids. Good results have been obtained with citric acid, phosphoric acid and propionic acid singly or in a mixture. 5.0 to 0.01 per cent of acid by weight of that of the biosynthetic pesticide products is generally used.

The compositions according to the invention can also contain substances having a fungicidal or fungistatic action. Good results have been obtained with methyl parahydroxybenzoate, ortho-phenylphenol and propionic acid, it being possible for these to be used singly or in a mixture. They are generally used at a rate of 0.0001 to 1.0 per cent by weight of that of the biosynthetic pesticide products.

The compositions according to the invention are advantageously in the form of a suspension of solid particles of biosynthetic pesticide products in a liquid. These suspensions generally contain from 2 to 40% by weight and, more often, from 3 to 30% by weight of biosynthetic pesticide products and from 60 to 98% by weight and, more often, from 70 to 97% by weight of liquid.

The present invention also relates to processes for the manufacture of the compositions according to the invention.

The substance according to the invention is used, to form the compositions according to the invention, at any stage in the manufacture of the biosynthetic pesticides or their possible precursors or in the manufacture of the compositions according to the invention, as long as it is later than the fermentation of the microorganisms which generate the said pesticides.

A process which is suitable for the manufacture of the compositions according to the invention consists in removing the culture medium of the microorganisms generating the biosynthetic pesticide products, and in separating the water from this by conventional techniques of water separation such as centrifugation, ultrafiltration, precipitation by addition of a non-solvent such as acetone, or flocculation in such a way as to obtain a paste.

In the case of Bacillus thuringiensis and Bacillus sphaericus, the culture medium is removed for example at the end of the sporulation phase.

Another process consists in separating, from the culture medium of the microorganisms generating bio-synthetic pesticide products, and at the end of the sporulation phase, fractions which are rich in endotoxins or in spores or in these two products simultaneously. These fractions are then treated according to the same techniques as those used for the treatment of the pastes.

In order to obtain compositions in the form of dry powders, the paste thus obtained is dried by conventional techniques such as spray drying, drying by lyophilization, or drum drying in such a way as to obtain solid particles containing in general less than 15% and, preferably, less than 12% of water.

Another technique consists in adding the substance and the other possible additives to the paste before drying it and in subjecting the mixture to drying by one or other of the techniques indicated above.

In order to obtain the compositions according to the invention in the form of suspensions, the solid pesticide particles can be dispersed in a liquid phase which preferably contains water and which additionaly contains the substance as well as the other possible additives, in order to form a cream.

Another technique consists in incorporating, into the paste obtained after separation of water from the fermentation medium, the substance, optionally in the form of a concentrated solution, as well as the other possible additives.

The present invention also relates to a process for the use of the compositions.

The compositions according to the invention can be used as pesticides and, more particularly, as agents for eliminating insects at any stage of their development. To this end the compositions are sprayed onto the infected surfaces, plants, rivers, streams and any expanse of water by all methods which are known per se, such as spraying by hand, mechanical spraying and, more particularly, aerial spraying. They can be sprayed especially onto the surfaces infected by insects and, more particularly, by Lepidoptera, Diptera, Coleoptera, Aphaniptera, Orthoptera, Isoptera and Homoptera.

The doses to be employed depend on the biosynthetic pesticide used and the pathogenic agent to be eliminated.

In the case of Bacillus thuringiensis and Bacillus sphaericus, 50 to 5000 g of solid particles are generally sprayed per hectare. The compositions according to the invention can be sprayed as such when they are in the form of suspensions. They can also be dispersed, diluted or emulsified in a diluent such as water or an organic diluent such as a product of crude oil distillation (for example gas oil). In this case they are diluted by 1 to 300 times, usually 2 to 120 times and, preferably, 4 to 60 times their volume of diluent.

The examples which follow serve to illustrate the invention.

EXAMPLE 1

To the product obtained during the culturing of Bacillus thuringiensis serotype 3a3b after sporulation there are added 0.4 per cent of a 25% solution of ortho-phenylphenol in methanol, then 0.2 per cent of citric acid in powder form.

The pH of this product is adjusted to 4 by addition of phosphoric acid.

The product thus obtained is concentrated to give a paste containing about 15% of dry matter.

The insecticidal activity of this paste is measured using Anagasta kuhniella Z. according to the biological titration method of L. Charmoille et al. (Phytiatrie - Phytopharmacie, 1974, 23, p. 223-234).

Into 61 l of methanol there are mixed 23 kg of methyl parahydroxybenzoate and 21 kg of an aqueous solution containing 33% of 1,2-benzisothiazolin-3-one, then 11 kg of a surfactant (ethylene oxide on alkyl phenol).

6.7 l of this mixture are added per m$^3$ of paste.

The composition thus obtained has an insecticidal activity identical to that of the paste.

It is stored at ambient temperature for 6 months.

A stability study is carried out.

No release of unpleasant odour is observed, and the vessel containing the composition is not deformed.

The insecticidal activity has been preserved.

EXAMPLE 2

A product obtained by fermentation of Bacillus thuringiensis, serotype 14, is treated like the product described in Example 1.

The activity of the composition obtained is measured using Aedes aegypti according to the biological titration method of H. de Barjac and I. Larget, WHO-VBC79.744.

The composition is stored at ambient temperature.

The stability study shows that the composition has retained all its insecticidal activity over the course of 18 months; no release of unpleasant odour is observed during this period of time; the colour of the composition has remained stable.

EXAMPLE 3

A product obtained by fermentation of Bacillus thuringiensis serotype 3a3b is treated in a similar manner to the product described in Example 1. This product contains about 15% of dry matter.

The stability study shows that the composition has retained all its insecticidal activity over the course of 15 months at ambient temperature; no release of gas or unpleasant odour is observed, and the colour has not changed.

EXAMPLE 4

A product obtained by fermentation of Bacillus thuringiensis serotype 3a3b is treated, after sporulation, like the product described in Example 1.

There are then added, to the composition obtained, 3% by weight of sodium chloride, 0.2% by weight of propionic acid, 0.2% by weight of sorbic acid and 44.8% by weight of an aqueous concentrate containing 70% of sorbitol.

The vessels containing this composition showed no deformation after 6 months of storage at ambient temperature.

The insecticidal activity was measured after 1 month and 6 months of storage at ambient temperature; no significant variation was observed.

EXAMPLE 5

To the product obtained by fermentation of Bacillus sphaericus serotype 5a5b, after sporulation, there are added 0.4 per cent of a 25% solution of ortho-phenylphenol in methanol, then 0.2 per cent of citric acid in powder form. The pH of this product is adjusted to 4 by addition of concentrated phosphoric acid.

The product thus obtained is concentrated to give a paste containing about 12% of dry matter.

Into 61 l of methanol there are mixed 23 kg of methyl parahydroxybenzoate, 11 kg of surfactant (ethylene oxide on alkyl phenol) and 21 kg of an aqueous solution containing 33% of 1,2-benzisothiazolin-3-one.

6.7 l of this mixture are added per $m^3$ of paste.

The composition thus obtained is stable over the course of time.

The vessels containing this composition did not show any deformation after 15 months of storage at ambient temperature. The colour of the composition is stable, and no blackening is observed.

The insecticidal activity is measured on Culex pipiens. After 15 months of storage no significant variation is observed.

A count was carried out on Petri dishes incubated for 24 hours at 30° C.; at the time of the preparation the composition contained $2.1 \times 10^7$ viable spores per mg and, after 15 months, $2.4 \times 10^7$ viable spores per mg.

EXAMPLE 6

A product obtained by fermentation of Bacillus thuringiensis serotype 7, after sporulation, is treated like the product described in Example 1.

A count of viable spores is carried out on Petri dishes which contain an gelose nutrient medium, favourable to the germination of the spores and to the growth of the bacteria, and which are incubated for 24 hours at 30° C. At the time of the preparation of the composition, it contained $1.3 \times 10^7$ spores per mg. 10 months later the number of spores had not varied, no release of gas was observed, and no blackening was recorded.

EXAMPLE 7R (comparison)

A product obtained by fermentation of Bacillus thuringiensis serotype 3a3b is centrifuged after sporulation, and then adjusted to a pH equal to 4 by addition of citric acid.

To the paste thus obtained there is added 0.3 per cent of an amphoteric, surface-active disinfectant containing heavy-molecule amino acids (trademark Tego 103 G).

After 13 days of storage at 30° C., the vessel containing this sample exhibits swelling, and the product releases an unpleasant odour and begins to blacken.

EXAMPLE 8 AND COMPARISON EXAMPLES 9R AND 10R

A product obtained by fermentation of Bacillus thuringiensis sertoype 3a3b is centrifuged, after sporulation, and the pH is then set: one sample is set at pH 7.4; and another sample at pH 6 with citric acid.

There are then added to each of these samples:

for Example 8 according to the invention:

0.2 per cent of an aqueous solution containing 33% of 1,2-benzisothiazolin-3-one and 0.1 per cent of an aqueous solution containing 22% of 2,6-di-tert-butyl-4-methylphenol (BHT);

for comparison Example 9R:

0.6 per cent of an aqueous solution containing 10% of chloracetamide and 0.1 per cent of an aqueous solution containing 22% of 2,6-di-tert-butyl-4-methylphenol (BHT);

for comparison Example 10R:

no additional ingredient.

These different products are stored at 25° C. and their stability is observed over the course of time. The criteria used are as follows: production of gas, presence of contaminants by microscope observation, deformation of the flask containing the sample, blackening of the sample. The storage life is assessed using one of these criteria. The test was finished after 100 days.

The results are given in Table 1.

TABLE 1

| Examples | 9 | | 10R | | 11R | |
|---|---|---|---|---|---|---|
| pH | 7.4 | 6 | 7.4 | 6 | 7.4 | 6 |
| storage life in days | 100 | 100 | 3 | 8 | 3 | — |

—not determind

EXAMPLE 11 AND COMPARISON EXAMPLE 12R

To the product obtained by fermentation of Bacillus thuringiensis serotype 14, after sporulation, there is added 0.2 per cent of citric acid in powder form, then the pH of the product obtained is adjusted to 4 with 42% phosphoric acid.

This product is centrifuged in order to obtain a concentrated paste.

No additional ingredient is added to the sample of comparison example 12R.

To the paste corresponding to the sample of Example 11 according to the invention there are added 6.7 l/m$^3$ of the alcoholic mixture containing 1,2-benzisothiazolin-3-one as described in Example 1.

After 16 months of storage at ambient temperature, the paste of Example 12R exhibits a release of gas and the flask containing it is deformed; whereas the paste of Example 11 has not evolved and is stable, and the flask containing it is not deformed.

EXAMPLE 13 AND COMPARISON EXAMPLE 14R

To the product obtained by fermentation of Bacillus thuringiensis serotype 14, after sporulation, there is added 0.2 per cent of a 25% methanolic solution of orthophenylphenol.

The pH of this composition is 8.2.

To the composition corresponding to the sample of Example 13 according to the invention there are added 6.7 l/m$^3$ of the alcoholic mixture containing the 1,2-benzisothiazolin-3-one as described in Example 1.

No ingredient is added to the sample of comparison Example 14R.

After 6 months of storage at 25° C., the composition of Example 14R has become black and the flask containing it is deformed; the composition of Example 13 has a normal colour and the flask containing it is not deformed.

We claim:

1. A composition containing a biosynthetic pesticide product non-toxic to warm-blooded and cold-blooded animals derived from a microorganism of the family Bacillaceae microorganism not to include vegetative cells of said microorganism itself as said pesticide in the form of solid particles in suspension in a liquid, comprising at least one substance of general formula (I):

in which R represents a hydrogen atom, a halogen atom, or a salt deriving from this substance.

2. The composition according to claim 1, wherein in formula (I) R represents hydrogen, chlorine, bromine, or an alkaline metal salt of formula (I) such as a sodium or potassium salt, an ammonium salt or a salt of an organic base.

3. The composition according to claim 1, wherein the substance is 1,2-benzisothiazol-3-one.

4. The composition according to claim 1, wherein the pH of the compositions is between about 3.5 and 8.5.

5. The composition according to claim 4, wherein the pH of the compositions is situated in acid pH zones of between about 3.5 and 6.5.

6. The composition according to claim 4, wherein the pH of the compositions is situated in neutral pH zones of between about 6.5 and 7.5.

7. The composition according to claim 4, wherein the pH of the compositions is situated in basic pH zones of between about 7.5 and 8.5.

8. The composition according to claim 1, wherein they contain from 0.0001 to 0.1 percent of the substance of general formula (I).

9. The composition according to claim 1, wherein they contain at least one of methyl parahydroxybenzoate, ortho-phenylphenol, or citric acid.

10. The composition according to claim 1, wherein the biosynthetic pesticide product originates from Bacillus thuringiensis or Bacillus sphaericus.

11. A process for the manufacture of compositions according to claim 1, wherein the culture medium of the microorganisms is removed, the water is separated from it in such a way as to obtain a paste, and the substance of general formula (I) is incorporated into it.

12. A process for eliminating insects, wherein a composition according claim 1, is sprayed onto infected surfaces.

* * * * *

REEXAMINATION CERTIFICATE (3166th)

United States Patent [19]

Gago et al.

[11] B1 4,915,943

[45] Certificate Issued Apr. 1, 1997

[54] COMPOSITIONS CONTAINING BIOSYNTHETIC PESTICIDE PRODUCTS, PROCESSES FOR THEIR PRODUCTION AND USE

[75] Inventors: Ignace Gago, Braine-l'Alleud; Lucien Charmoille, Brussels; Rene Detroz, Ohain, all of Belgium

[73] Assignee: Novo Nordisk A/S, Bagsvaerd, Denmark

Reexamination Request:
No. 90/004,091, Jan. 5, 1996

Reexamination Certificate for:
Patent No.: 4,915,943
Issued: Apr. 10, 1990
Appl. No.: 244,384
Filed: Sep. 14, 1988

[30] Foreign Application Priority Data

Sep. 14, 1987 [FR] France .................... 87 12738

[51] Int. Cl.$^6$ .................... A61K 35/74; A61K 31/025
[52] U.S. Cl. .................... 424/93.46; 424/93.461; 424/93.462; 514/373; 435/170
[58] Field of Search .................... 424/93.46, 93.461, 424/93.462; 514/373; 435/170

[56] References Cited

U.S. PATENT DOCUMENTS 4,062,946  1/1977  Law .

FOREIGN PATENT DOCUMENTS 184159  8/1978  Czechoslovakia .

OTHER PUBLICATIONS

Gu, "Stability of Crystal Toxin of *Bacillus thuringiensis* and the Methods for Preservation of the Fermenting Liquor", Weishenqwuxue Tongbao 11(5):193–195 (1984) Abstract CA102:144796.

Technical Information Bulletin Z10–13, Feb. 1980, Formally ICI Americas Inc. (Zeneca Biocides) Wilmington, DE.

Technical Information Bulletin Z10–15, Feb. 1985, Formally ICI Americas Inc. (Zeneca Biocides) Wilmington, DE.

Technical Information Bulletin Z10–18, Oct. 1984, Formally ICI Americas Inc. (Zeneca Biocides) Wilmington, DE.

*Primary Examiner*—Jean C. Witz

[57] ABSTRACT

The compositions contain a biosynthetic pesticide product, preferably originating from microorganisms of the genus Bacillus, in suspension in a liquid and at least one substance of general formula:

$$R-\underset{}{\underset{}{\bigcirc}}\begin{array}{c}S\\\diagdown\\NH\\\diagup\\CO\end{array} \quad (I)$$

in which R represents a hydrogen atom, a halogen atom, or a salt derived from this substance.

The substance has a bacteriocidal or bacteriostatic action.

The compositions are effective against insects.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–12 is confirmed.

* * * * *